(12) United States Patent
Sluijter et al.

(10) Patent No.: US 9,162,075 B2
(45) Date of Patent: Oct. 20, 2015

(54) USE OF PULSED RADIO FREQUENCY

(75) Inventors: Menno Emanuel Sluijter, Kerns (CH); Alexandre Jose Leonardo Teixeira, Oporto (PT)

(73) Assignee: HITOPS GMBH, Kerns (CH)

( * ) Notice: Subject to any disclaimer, the term of this patent is extended or adjusted under 35 U.S.C. 154(b) by 0 days.

(21) Appl. No.: 13/518,225

(22) PCT Filed: Dec. 23, 2010

(86) PCT No.: PCT/NL2010/050886
§ 371 (c)(1),
(2), (4) Date: Oct. 8, 2012

(87) PCT Pub. No.: WO2011/078676
PCT Pub. Date: Jun. 30, 2011

(65) Prior Publication Data
US 2013/0079835 A1  Mar. 28, 2013

(30) Foreign Application Priority Data

Dec. 23, 2009  (WO) ................ PCT/NL2009/050800

(51) Int. Cl.
*A61N 1/05* (2006.01)
*A61N 1/40* (2006.01)
*A61N 1/06* (2006.01)
*A61N 5/00* (2006.01)

(52) U.S. Cl.
CPC  *A61N 1/40* (2013.01); *A61N 1/056* (2013.01); *A61N 1/06* (2013.01); *A61N 5/00* (2013.01)

(58) Field of Classification Search
CPC ........... A61N 1/06; A61N 1/40; A61N 1/056; A61N 5/00

USPC .......................................... 607/3, 2
See application file for complete search history.

(56) References Cited

U.S. PATENT DOCUMENTS

| | | | |
|---|---|---|---|
| 5,540,681 A * | 7/1996 | Strul et al. | 606/34 |
| 6,464,680 B1 * | 10/2002 | Brisken et al. | 604/501 |
| 2005/0288730 A1 | 12/2005 | Deem et al. | |

(Continued)

FOREIGN PATENT DOCUMENTS

| EP | 1 916 018 | 4/2008 |
|---|---|---|
| EP | 1916018 A1 * | 4/2008 |

OTHER PUBLICATIONS

Wissniowski, Thadaus, et al. "Activation of Tumor-specific T Lymphocytes by Radio-Frequency Ablation of the VX2 Hepatoma in Rabbits". Oct. 1, 2003. Cancer Research. 63. 6496-6500.*

(Continued)

*Primary Examiner* — Christopher D Koharski
*Assistant Examiner* — Michael Carey
(74) *Attorney, Agent, or Firm* — Thompson Hine LLP

(57) ABSTRACT

The invention relates to a method for medical treatment of a mammal, preferably a human, by applying pulsed radiofrequency (PRF) stimulation intravascularly. More particularly, said method has as effect that it boosts the immune system and/or that it relieves pain. In a preferred embodiment, the disease or condition to be treated is caused or accompanied by immunodeficiency, more preferably the disease or condition is selected from the group of cancer, infectious diseases, immunosuppression or otherwise caused immunodeficiencies. Also auto-immune diseases and conditions associated with allostatic load are preferred for treatment with the method of the invention. In an also preferred embodiment, the PRF stimulation is applied together with vaccination.

22 Claims, 1 Drawing Sheet

1. VENFLON-TYPE IV NEEDLE, 18 OR 20 G

2. INNER NEEDLE REMOVED, DOUBLE STOPCOCK ATTACHED

3. THE METAL COIL

4. COIL INTRODUCED, GUIDED BY IMPEDANCE

(56) References Cited

U.S. PATENT DOCUMENTS

2006/0178703 A1\* 8/2006 Huston et al. .................. 607/2
2008/0027505 A1   1/2008 Levin et al.
2008/0051854 A1\* 2/2008 Bulkes et al. ................. 607/60

OTHER PUBLICATIONS

Wissniowski, Thadeus et al. "Activation of Tumor-specific T Lymphocytes by Radio-Frequency Ablation of the VX2 Hepatoma in Rabbits". Oct. 1, 2003. Cancer Research. 63. 6496-6500.\*

International Search Report for PCT/NL2010/050886, date of mailing Apr. 26, 2011.
Zheng et al. "Electrode Impedance: An Indicator of Electrode-Tissue Contact and Lesion Dimensions During Linear Ablation," Journal of Interventional Cardiac Electrophysiology, vol. 4, No. 4 (2000), pp. 645-654.
Sluijter et al. "Intra-articular Application of Pulsed Radiofrequency for Arthrogenic Pain—Report of Six Cases," Pain Practice, vol. 8, No. 1 (2008), pp. 57-61.
Cleary et al. "Effect of isothermal radiofrequency radiation on cytolytic T lymphocytes," The FASEB Journal, vol. 10, No. 8 (1996), pp. 913-919.

\* cited by examiner

1. VENFLON-TYPE IV NEEDLE, 18 OR 20 G
2. INNER NEEDLE REMOVED, DOUBLE STOPCOCK ATTACHED
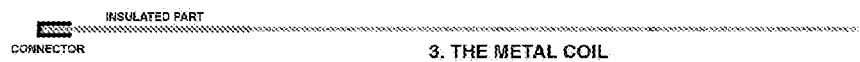
INSULATED PART
CONNECTOR    3. THE METAL COIL
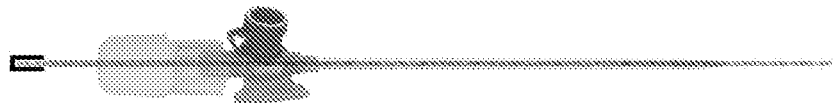
4. COIL INTRODUCED, GUIDED BY IMPEDANCE

USE OF PULSED RADIO FREQUENCY

RELATED APPLICATIONS

This application is a National Phase of co-pending International Application No. PCT/NL2010/050886 filed Dec. 23, 2010, which claims priority to International Patent Application No. PCT/NL2009/050800 filed Dec. 23, 2009.

FIELD OF THE INVENTION

The invention relates to the field of medicine, more particularly the field of treatment with electrical signals.

BACKGROUND OF THE INVENTION

Use of electrical current, especially in the area of anodynia, more specifically in the area of pain relief, has been known for several decades. The first reports of the use of electrical current for pain management appeared in the 1930's. Initially, DC was used to induce lesions of nerves through the temperature increase caused by the electrical current (thermocoagulation). Later, this has been replaced by AC with a frequency of 400 to 500,000 Hz, which has been shown to deliver more precise lesions. In the past few decades this radiofrequency (RF) thermocoagulation has been established as an accepted treatment option for trigeminal neuralgia, for unilateral cancer pain and for zygoapophyseal joint pain. Further, RF has been used in other fields:

- in cardiology for thermocoagulation of conductive tissue in the heart that conduct aberrant stimulus patterns;
- in oncology for destroying tumor tissue;
- in orthopedics for treatments of cartilage defects in osteoarthritis.

The therapeutic effect was mainly concerned with the destruction of tissue by the heat that was generated by the current. The development of a novel method for administrating high frequency current, pulsed radiofrequency (PRF) allowed using it to treat other pathologies and nerve structures. With PRF, current is delivered in pulses of short duration (1-100 msec) separated by a silent period of about 0.1 to 1 sec. Output current may be set not to exceed 42° C. to prevent cell destruction. Heat generated by the application of the current is dissipated between pulses. Nowadays PRF is recognised as treatment for e.g. various forms of spinal and facial pain and peripheral neuralgias.

The mechanism through which PRF causes long-lasting pain relief when applied in the vicinity of a nerve is not known.

In the meantime, it has been published by the present inventors (WO 2008/094042) that PRF has beneficial effects on seeds and the germination of seeds. Although also the mechanism that causes these effects is not yet elucidated, it appears that PRF is capable of influencing biological tissue to perform better.

Except for pain relief no further clinical therapies involving PRF have been established.

SUMMARY OF THE INVENTION

The present invention now relates to a method for medical treatment of a mammal, preferably a human, by applying pulsed radiofrequency (PRF) stimulation intravascularly. Preferably by such a method the immune system is boosted and/or pain is relieved.

In a preferred embodiment, the disease or condition to be treated is caused or accompanied by immunodeficiency, more preferably the disease or condition is selected from the group of cancer, infectious diseases, immunosuppression or otherwise caused immunodeficiencies. Also auto-immune diseases and conditions associated with allostatic load are preferred for treatment with the method of the invention. In an also preferred embodiment, the PRF stimulation is applied together with vaccination. Also part of the invention is the use of intravascular PRF or PRF, which is applied intravascularly, in therapy, preferably in the therapy of immunodeficiency, more particular in the therapy of cancer, and in the therapy of auto-immune diseases, such as rheumatoid arthritis, COPD, multiple sclerosis, Crohn's disease, and the therapy of conditions associated with allostatic load, such as diabetes and pathologies caused by diabetes, post-traumatic conditions, fibromyalgia, chronic fatigue syndrome, burnout, migraine, depression, dementia, osteoporosis and osteoarthritis.

LEGENDS TO THE FIGURES

FIG. 1. Example of an electrode usable with the current invention.

DETAILED DESCRIPTION

PRF (pulsed radiofrequency) is a clinically proven method to alleviate pain in cases where pain sensation is due to or transported via peripheral nerves (such as in case of pain caused by pinching a nerve by a slipped disc of the spinal column, facial pain, trauma, etc.). As discussed above, PRF, just like RF, works through applying an electrical AC current to the vicinity of a nerve. Usually a frequency of 400.000-500.000 Hz is used, but the range may vary from 50.000 to 1.000.000 Hz. In PRF, in contrast to continuous RF, the heat that is generated at the tip of the electrode during the active phase of the duty cycle is dissipated during the resting phase of zero, or of appreciably lower voltage. The settings of the current generator should be adjusted so that the mean temperature around the electrode tip does not rise to cell destructive levels, which start from 45° C. upwards. It is allowable that the temperature may briefly rise above 45° C. during the active phase of the duty cycle (the so-called heat spikes), although the biological effects of these ultrashort rises in temperature are not known. However, the spread of heat into the tissues during a heat spike has been predicted to be minimal (<0.2 mm), thereby outruling that a thermal (coagulation or neurotomy) effect is the cause of the clinical efficacy of PRF nerve treatment—at the same time also casting doubts whether the thermal effect would be crucial for RF. As for yet, there is no conclusive theory explaining and supporting the observed effects of PRF in the alleviation of pain.

PRF (and RF) have been shown to be only effective if the electrical current is applied near the tissue to be treated. This is understandable, since the current density, and therefore the electric field, will rapidly fall off as the distance to the electrode increases. The same will apply to the heat generated in RF. The tissue in which a biologically active electric field is generated will thus be small (about 2-8 mm for a voltage of 45 Volts).

In contrast with this general accepted placing of the electrode in the vicinity of the tissue to be treated, it has now been found that overall beneficial effects can be obtained by applying PRF intravascularly. Although no theoretical explanation of the observed effects can yet be given, it is assumed that the electrical current that is delivered through the electrode in a blood vessel is transported through the vessel. The electrical resistance of the vessel wall is 200 times as large as that of the blood, which means that the blood vessel can be regarded as an insulated electrical cable. Although the electrical resistance of the blood wall vessel will vary according to the type and diameter of the blood vessel, in general venous blood vessel walls will have a resistance of about 20 to 1000Ω cm², where the lower resistance is found in blood vessels where much transport over the vessel wall is taking place (e.g. in muscle veins, Olesen & Crone, 1984, Biophys. J. 42:31-41) and the higher values occur in vessels of the blood brain barrier (Butt et al., 1990, J. Physiol. 429:47-62).

One of the theories is that the effect of the intravascular PRF treatment is a general boost of the (cells of the) immune system. A similar effect has been found in plant seeds (see WO 2008/094042) and tissue culture (see PCT/NL2009/050483), where upon PRF stimulation the vigour of the treated cells was increased, and in intra-articular PRF (see WO 2008/069647) where the pain effective treatment would also involve lymphoid cells. Apparently, the PRF treatment when applied in the blood vessels is thought to be able to stimulate the blood lymphocytes and make them more active. Another possible explanation is derived from U.S. Pat. No. 6,038,478, in which it is disclosed that electrical stimulation is able to attract lymphocytes. However, in this document frequencies of less than 1000 Hz were used and stimulation was only applied to brain tissue. Further, the use of electrical stimulation to promote bone and soft tissue healing is known (see e.g., J. Black, Clin. Plast. Surg Apr. 12, 1885 (2):243-57).

In another theory, the intravascular PRF treatment is thought to affect the nervus vagus. The vagus nerve (cranial nerve X) has recently been identified as a pathway that impacts on inflammation. The key endogenous mediator of this so-called cholinergic anti-inflammatory pathway is acetylcholine, the principal neurotransmitter of the vagus nerve, which specifically interacts with α7 cholinergic receptors expressed by macrophages and other cell types to inhibit tumor necrosis factor (TNF) production (Tracey KJ. The inflammatory reflex. Nature 2002;420:853-9.). Stimulation of the vagus nerve has been suggested by Giebelen (Thesis, University of Amsterdam, 2008) to be effective in the treatment of inflammatory, more especially, TNF-α mediated diseases, such as Crohn's disease, rheumatoid arthritis and sepsis. However, in this last study the nervus vagus was electrically stimulated by direct application of electrical current with a very low frequency (1 Hz) on the nerve. One additional argument for this last theory resulted from our experiments. In one of the patients it was impossible to use the vena brachialis for introduction of the electrode. Instead, one of the veins on the back of the hand was used.

Although the actual administration of the electrical field through PRF was essentially similar, no results of the treatment were found. A possible explanation in view of the vagus nerve theory can be that the distance to this nerve was made larger by using the hand veins in stead of the vena brachialis, resulting in less electrical field to arrive at the vagus nerve and/or nucleus tractus solitarius.

The observed effect on immune cells and inflammation in general means that the PRF treatment can be effective in those conditions or diseases where the immune system is affected. Such conditions are, for example, infectious diseases, in particular viral infections, and more specifically HIV infection; cancer, comprising solid tumours and blood borne tumours, such as lymphoma's, myeloma's, leukemia, breast cancer, lung cancer, head-and-neck cancers, colon cancer, pancreas cancer, prostate cancer, gastric cancer, ovarian cancer, etc.; immunosuppression, caused by chemotherapy, radiation therapy, or treatment with corticosteroids; immunedeficiency, e.g. caused by malnutrition, ageing, cancer, viral infections or (hereditary) primary immunedificiencies like SCID, ADA deficiency, Di George's syndrome, Omenn syndrome, agammaglobulinemia, Wiskott-Aldrich syndrome, ataxia telangiectasia, ataxia-like syndrome, Nijmegen breakage syndrome, Bloom syndrome, etc.; complement deficiencies; and phagocyte disorders, such as Kostmann syndrome, neutropenia, and the like.

Further, auto-immune diseases, such as rheumatoid arthritis, alopecia areata, ankylosing sponmdylitis, autoimmune cardiopathy, autoimmune hepatitis, autoimmune pancreatitis, autoimmune inner ear disease, autoimmune progesterone dermatitis, autoimmune uveitis, Chagas disease, chronic obstructive pulmonary disease (COPD), celiac disease, cold agglutinin disease, Crohn's disease, dermatomyositis, diabetes mellitus, eosinophilic fasciitis, gastrointestinal pemphigoid, Goodpasture's syndrome, Graves' disease, Guillain-Barré syndrome, Hashimoto's encephalitis, Hashimoto's thyroiditis, thrombocytopenic purpura, irritable bowel syndrome (IBS), Kawasaki's disease, lupus erythematosus, Miller-Fisher syndrome, mixed connective tissue disease (MCTD), morphea, multiple sclerosis, myasthenia gravis, narcolepsy, neuromyotonia, pemphigus vulgaris, pernicious anaemia, polymyositis, primary biliary cirrhosis, inflammatory neuropathy, psoriasis, psoriatric arthritis, relapsing polychondritis, restless leg syndrome, sarcoidosis, schizophrenia, giant cell arthritis, ulcerative colitis, vaculitis, vitiligo and Wegner's granulomatosis can benefit from a treatment with PRF as herein disclosed.

Also diseases which relate to an (increased) allostatic load, such as insulin resistance, metabolic syndrome, diabetes type 2, atherosclerosis, hypertension, coronary infarction, stroke, migraine, cognitive dysfunctions, depression, burn-out, chronic fatigue syndrome, fibromyalgia, post-traumatic stress syndrome, post-traumatic vegetative syndromes, strees related sleep disorders, arthrosis, gastric ulcers, neuropathies, etc. can be subject to PRF treatment.

Especially included are any diseases in which an elevated CRP level is found, such as dementia (Alzheimer's disease) and mental diseases (including depression, psychosis, stress related disorders, etc.).osteoporosis and chronic inflammations, whether auto-immune or not, such as rheumatoid arthritis. and ulcerative colitis.

PRF can also be given in connection with vaccination, thereby enhancing the antibody response to the antigen. Preferably, therefore, in this case the PRF treatment is applied some time after the (first) vaccination as a booster treatment, or before vaccination to sensitize the immune system.

Especially preferred is the use of PRF in the treatment of cancers, both solid cancers and lymphoma's, leukemia or myeloma's, both since these conditions cause immunodeficiency (which is ameliorated by the PRF stimulation) and because the immune system is able to attack tumor cells. Further preferred is PRF therapy for cancers that have developed metastases. In cancer, PRF treatment is an excellent additional treatment next to chemotherapy or radiotherapy, since it ensures a stimulation of the immune system, which otherwise would be impaired by the chemical or radiation treatment.

It goes without saying that PRF can be used in combination with the chemical or other treatment that the patient otherwise also would have received, like medication, radiation treatment, etc.

The instruments for applying PRF to a patient comprise a needle-like electrode, connected to a PRF current source and a means for providing connection to earth. The PRF current source (or lesion-generator) will provide, next to the source for the current, also a stimulator function, to check for the proper positioning of the electrode, and the facility of measuring the impedance of the circuit between patient, earth and apparatus. These devices are commercially available (e.g. the NT 2000 Radiofrequency Lesion Generator from Neurotherm, USA) The procedure to apply intravascular PRF is easy to perform and does not need special skills. For intravascular PRF an insulated needle with an exposed tip of minimally 5 mm, but preferably 15-20 mm, is inserted into a blood vessel, preferably a vein. With such a needle the impedance of the system should be below 1000Ω, preferably about 100-600Ω, more preferably about 200-250Ω. Any blood vessel of sufficient size can be used, but preferred are venous blood vessels that are easily accessible, such as the blood vessel in the elbow (vena brachialis), in the thigh (vena saphena) or neck (vena jugularis). Preferably, in view of the role of the nervus vagus in the inflammatory reflex, a vein should be used which provides a minimal distance to the nervus vagus, such as the vena brachialis, the vena brachiocephalica or the vena jugularis.

In the prior art (e.g. US 2005/0288730), beneficial effects have been described for intravenous pulsed electrical field (PEF) stimulation of the renal nerve or other non-renal nervous structures, where a PEF catheter is navigated through the veins to come close to the target nerve or neuronal structures. The goal of this stimulation was electroporation (i.e. denervation) or neuromodulaton of the renal nerve (or neuronal structures belonging to the cardiac-renal system) to treat congestive heart failure, hypertension, renal system diseases and other renal anomalies. To achieve such effects, this prior art document uses very high filed strengths, up to 10,000 V/cm. However, the present application is not related with electroporation, denervation or neuromodulation of the renal nerve or neural structures belonging to the cardiac-renal system (other than the nervus vagus) and generally uses lower field strengths to prevent tissue damage.

When the electrode is in the proper position and connected to the PRF current source, the patient will be connected to earth (e.g. by a so-called earth-plate) to establish an electrical circuit. Exposure to PRF is then applied. Usual values are a pulse duration of 10 msec and a pulse frequency of 2-5/sec; a voltage of 20-80 V depending on the impedance of the system; and a total duration of treatment of 10-30 minutes. There is however a wide variation in parameters that may be used:

Frequency: 50.000-1.000.000 Hz, preferably 150.000-500.000 Hz

Pulse duration: 0.1-100 msec, preferably 5-20 msec.

Pulse frequency: 1-20/sec, preferably 2-5/sec

Voltage: 10-80 V, preferably 40-60 V

Treatment time: 2-30 minutes

Further the duty cycle may be irregular, with varying pulse duration and pulse frequency, and the voltage may not be brought back to zero during the rest phase.

The PRF treatment is painless (except for the initial insertion of the needle electrode) and no adverse reactions have thus far been observed. In otherwise healthy persons apparent changes take place.

The treatment has also been tried in patients with Complex Regional Pain

Syndrome and this effected in a disappearance of pain and allodynia for a short period (a few hours). It would thus be usable in this patient group as an additional treatment, e.g. to accommodate further treatments and make these more acceptable to the patients, especially in those situations where the allodynia is prohibitive for further handling the patient.

For intravascular placement of the electrode, the electrodes which are currently used for (P)RF are unsuitable since they have a very sharp tip, which could damage the blood vessel wall. Further, because of the nature of the blood vessel, the use of rigid instruments is limited. For this purpose, the invention also comprises an electrode for use in intravascular PRF. Basically such an electrode comprises a hollow outer (needle) part, optionally provided with a releasable inner stylet and an inner, true electrode part (or coil), see FIG. 1. The outer part is completely insulated, and the insulation material may be any non-conductive material which does not react with biological tissue, such as plastics like polyethylene, polypropylene and the like. For ease of penetration through the skin, the underneath tissues and the wall of the vein, it has a very sharp tip. If present, also the stylet, which fits into the hollow needle, may be as sharp-edged as the needle to construe a continuous sharp-edged tip. After perforation of the blood vessel wall, the stylet is removed. The inner part, the actual electrode, is then inserted into the needle and will extend from the hollow outer needle into the blood vessel. The electrode has a blunt end of more than 5 mm, preferably 15-25 mm, and consists mainly of conductive material, such as metal or doped conductive polymers. Preferably, the electrode is flexible to allow it to follow the natural curves and movements of the blood vessel.

Another option is insulation of the tip of the electrode. It is around the tip of the electrode that the electric and thermal fields are strongest, and in tissue applications of PRF electrodes it has been shown that these strong fields may cause a microscopically small area of necrosis around a sharp needle tip. This effect is already minimalised by the fact that in this case the electrode is blunt and residing in the blood stream, but if the tip will often lie very close to the blood vessel wall it is worth taking precaution. By insulating the tip any damage would be prevented or at least further reduced, without affecting the therapeutic effect of applying the PRF current.

In a further embodiment of the present invention, the electrode is an electro-catheter. Such a catheter can advantageously be used to enable placement of the active part of the electrode closer to a target. Such a target can be any structure in the body that qualifies for treatment of anatomically limited pathology, such as for example Crohn's disease and malignant tumors, or an anatomically limited target, such as for example structures in the central or peripheral nervous system. As discussed above, according to one of the theories underlying the efficacy of intravascular PRF, the electrical field should stimulate the nervus vagus. Placing the electro-catheter in a vessel within close proximity of this nerve would thus enable a more direct stimulation of the nerve and hence a more effective treatment. Some of the blood vessels that run quite close to the nervus vagus are the vena jugularis interna and the left or right innominate vein (brachiocephalic vein), and these veins thus seem an optimal place to position the electro-catheter.

The electro-catheter can be a conventional catheter, but it can also have a steerable tip, such as the catheter disclosed in WO 2010/113072. The catheter disclosed in this patent document would ideally be suited for the presently claimed method.

The RF Lesion Generators that are commercially available are suitable for performing this procedure. However, modifications would greatly facilitate this particular procedure. Particularly important is to ensure that the impedance of the system does not fall below 100Ω, because then the danger would exist that with voltages of 60V gas bubbles would be formed in the blood, which of course can lead to (life-threatening) emboli. Systems to limit the impedance and/or current output are known in the electro technical arts and can easily be applied to the commercially available radiofrequency current generators.

EXAMPLE 1

A male subject was diagnosed (on 31 Mar. 2009) with large cell undifferentiated lung carcinoma. There were glandular nodes in the mediastinum and a metastase in the adrenal gland. Normally the prospects of the disease in this stage are very poor: hardly reactive to chemo- or radiotherapy and a survival of a few months. The patient suffered from heavy back aches.

The subject was treated with intravascular PRF in the vena brachialis on Apr. 11, 2009. PRF parameters were 4 times per second pulses of 10 msec 420,000 Hz, 60 V for 20 minutes. In four weeks after PRF treatment back aches gradually disappeared and at four weeks chemotherapy was started, later complemented with radiotherapy. The patient was able to continue his daily work without problems and an MRI diagnosis in November 2009 showed a total disappearance of mediastinal ingrowth and absence of metastases.

Twenty months after treatment, the patient is diagnosed free of tumor and no signs of a relapse have occurred.

EXAMPLE 2

Diabetic Retinopathy Patient

In a 48 year old male patient diabetes mellitus type 2 was diagnosed 10 years ago. He was medicated with Metformin 1000 mg daily, up till 2007. Since then insulin was added to the therapeutic regimen for a better control of his blood sugar level. He was also treated for arterial hypertension with Irbesartan, an angiotensin II receptor antagonist and with Atorvastatin for hypercholesterolemia. As a consequence of the diabetes mellitus he developed diabetic retinopathy in both eyes.

In September 2008 he was operated for an acute narrow glaucoma of the right eye and after three unsuccessful surgical procedures over a 3 months period he became blind in the right eye. The left eye was submitted to laser photocoagulation in 2009.

This patient was presented in September 2010 for follow up after successful treatment for acute sciatic pain due to extruded discal hernias L4-L5 and L5-S1. Until that time the blood pressure and the serum cholesterol had been responding adequately to medication but the diabetes had remained uncontrolled. For diabetes he took 850 mg of Metformin daily and 14 units of insulin lente twice daily. This was supplemented with rapid insulin 3 times daily before meals based on a sliding scale. The mean monthly blood sugar measured in his pocket machine had been oscillating between 190 mg/l and 220 mg/dl over the last year, and his morning blood sugar ha been between 200 and 260 mg/dl in the same period on 75% of days with only 25% of the values between 160 and 200 mg/dl.

During his visit he inquired about any possible treatment to improve or retard the loss of vision of his remaining eye. The surgery in 2009 had been unsuccessful and the visual acuity had been deteriorating to 40%, with a loss of 20% over the last 8 months.

IV-PRF and its experimental nature were thoroughly discussed with him, and he decided to be submitted to the procedure. Treatment was aimed at retarding the progression of what the ophthalmologists considered to be a rapidly progressive visual loss.

IV-PRF was performed on Jan. 10, 2010. in the vena brachialis The impedance was 276 Ohms PRF was applied at 4×10 msec and 45 V for 20 minutes. There were no complications.

In the first 2 weeks after treatment there were no noted alterations but on day 15, the morning blood sugar dropped to 129 mg/dl and it remained at a level between 99 mg/dl and 257 mg/dl, with 75% of the readings now below 200 mg/l and 25% above that value. This was accompanied by a reduction of the requirement of rapid insulin of about 50%. On day 22 the patient had an episode of hypoglycaemia of 49 mg/dl, 3 hrs after injecting the before-lunch dose of insulin. He recognized the symptoms and treated himself taking sugar orally.

The last mean monthly blood sugar value on his machine was 177 mg/dl and the value over the last 2 weeks was 155 mg/dl. The Hb A1C (glycosylated hemoglobin) was 6.6% on 20, Nov. 2010 and 6.8% on 31, may 2010. His visual acuity is unchanged 10 weeks after the iv-PRF.

EXAMPLE 3

COPD Patient

A 66 year old woman had been complaining of shortness of breath and coughing since 8-10 years. She had been diagnosed with COPD. In 2009 her condition deteriorated and she was seen by a pulmonologist. Her FEV1 at that time was 53% of her VC, with little improvement after a bronchodilator, and her FEF25-75% was 0.59 L/sec (21% of normal).

Medication gave moderate relief, but on Mar. 4, 2010 her lung function showed no change: FEV1 57%, FEF25-75% 0.63 L/sec (22% of normal).

She requested to be treated with intravenous PRF. She was extensively informed about the experimental status of the procedure. The treatment was performed on Aug. 17, 2010. The impedance was 480 Ohms, PRF was applied at 4×10 msec/sec and 60 V, during 20 minutes. There were no complications.

Over the first 3 weeks after treatment there was a gradual but marked subjective improvement. On Sep. 15, 2010 her FEV1 was 68%. Her FEF25-75% had improved to 1.22 L/sec (44% of normal) before a bronchodilator and to 1.34 L/sec (48% of normal) after.

As advised by the pulmonologist she gradually stopped all medication. She keeps doing very well, now 4 months after treatment.

One further patient with COPD was treated and a subjective improvement is reported. No clinical pulmonological data after treatment are available yet.

EXAMPLE 4

Further Cancer Patients

Four other cancer patients have been treated in a similar way as the patients in the above examples. The condition of two patients (one renal epithelial carcinoma with generalized metastases in the bone; and one pancreas carcinoma with metastases in the liver) has improved after treatment, in one other patient (colon carcinoma with metastases in the brain) the treatment showed no effects. The fourth patient was only recently treated and no results are available yet.

EXAMPLE 5

Auto-Immune Disease Patients

Two patients with rheumatoid arthritis were treated as indicated above. In both a dramatic decrease of the CRP values (about 75% decrease) in the blood after treatment was observed. The CRP values started to increase again after about two months after treatment, but never reached more than 50% of the initial (pre-treatment) values.

One patient with multiple sclerosis was treated and clinical data are not yet available. The subjective improvement was exultating.

EXAMPLE 6

Allostatic Load

Next to the diabetes patient discussed in Example 2, a further diabetes patient was treated, with similar improvements in the insulin requirements as with the patient of Example 2.

One patient with a general, non-rheumatic osteoarthritis in hands and feet showed a clear improvement after treatment: the pain visual analogue scale (VAS) value decreased from 7 to 2.

Two patients with post-traumatic complaints (one complaining of pain after a femoral fracture and the other with vegetative complaints: lack of appetite, sleeping disorders) were treated and the (subjective) complaints decreased significantly.

The invention claimed is:

1. A method for medical treatment of a disease or condition in a mammal, the method comprising using a pulse generator for applying a plurality of pulsed radiofrequency (PRF) stimulations over a period of between 2 min and 30 min, the stimulations comprising applying a signal with a frequency of 50,000 Hz-1,000,000 Hz and a voltage of 10 V-80 V delivered in pulse bursts with a duration of 0.1 msec-100 msec and burst frequency of 1/sec-20/sec by an electrode with an impedance of less than 1000 Ω intravascularly to the mammal to medically treat the disease or condition, wherein the disease or condition and corresponding treatment result is selected from the group consisting of
- cancer and resulting in at least one of decreased mediastinal ingrowth, decrease in metastases, or decrease or absence of tumors;
- diabetes and resulting in at least one of decreased blood sugar levels or decreased insulin requirement;
- chronic obstructive pulmonary disease (COPD) and resulting in increased lung function;
- rheumatoid arthritis and resulting in decreased in C-reactive protein (CRP) levels; and
- osteoarthritis and resulting in decreased pain, wherein the medical treatment further results in activating the immune system or relieving pain and wherein PRF is applied together with vaccination.

2. The method according to claim 1, wherein the disease or condition to be treated is an inflammation related disease, an immune disease, an auto-immune disease or a disease related to allostatic load.

3. The method according to claim 2, wherein the disease or condition is selected from the group of cancer, infectious diseases, immunosuppression or immunodeficiencies.

4. The method according to claim 2, wherein the disease or condition is selected from the group of infectious diseases, in particular viral infections, and more specifically HIV infection; cancer, comprising solid tumours and blood borne tumours, such as lymphoma's, myeloma's, leukemia, breast cancer, lung cancer, head-and-neck cancers, colon cancer, pancreas cancer, prostate cancer, gastric cancer, ovarian cancer, and metastases thereof; immunosuppression, caused by chemotherapy, radiation therapy, or treatment with corticosteroids; immunodeficiency, e.g. caused by malnutrition, ageing, cancer, viral infections or (hereditary) primary immunodeficiencies like SCID, ADA deficiency, Di George's syndrome, Omenn syndrome, agammaglobulinemia, Wiskott-Aldrich syndrome, ataxia telangiectasia, ataxia-like syndrome, Nijmegen breakage syndrome, Bloom syndrome, etc.; complement deficiencies; and phagocyte disorders, such as Kostmann syndrome, neutropenia; auto-immune diseases, such as rheumatoid arthritis, alopecia areata, ankylosing sponmdylitis, autoimmune cardiopathy, autoimmune hepatitis, autoimmune pancreatitis, autoimmune inner ear disease, autoimmune progesterone dermatitis, autoimmune uveitis, Chagas disease, chronic obstructive pulmonary disease (COPD), celiac disease, cold agglutinin disease, Crohn's disease, dermatomyositis, diabetes mellitus, eosinophilic fasciitis, gastrointestinal pemphigoid, Goodpasture's syndrome, Graves' disease, Guillain-Barrésyndrome, Hashimoto's encephalitis, Hashimoto's thyroiditis, thrombocytopenic purpura, irritable bowel syndrome (IBS), Kawasaki's disease, lupus erythematosus, Miller-Fisher syndrome, mixed connective tissue disease (MCTD), morphea, multiple sclerosis, myasthenia gravis, narcolepsy, neuromyotonia, osteoporosis, pemphigus vulgaris, pernicious anaemia, polymyositis, primary biliary cirrhosis, inflammatory neuropathy, psoriasis, psoriatric arthritis, relapsing polychondritis, restless leg syndrome, sarcoidosis, schizophrenia, giant cell arthritis, ulcerative colitis, vaculitis, vitiligo, Wegner's granulomatosis; and conditions related to allostatic load like insulin resistance, metabolic syndrome, diabetes type 2, atherosclerosis, hypertension, coronary infarction, stroke, arthrosis, migraine, cognitive dysfunctions; stress related allostatic load conditions, such as depression, burn-out, chronic fatigue syndrome, fibromyalgia, post-traumatic stress syndrome, stress related sleep disorders, gastric ulcers; and trauma related allostatic load conditions, such as post-traumatic vegetative syndromes, neuropathies, phantom pain and unexplained persistent pain following trauma.

5. A method for medical treatment of a disease or condition in a mammal, the method comprising using a pulse generator for applying a plurality of pulsed radiofrequency (PRF) stimulations over a period of between 2 min and 30 min, the stimulations comprising applying a signal with a frequency of 50,000 Hz-1,000,000 Hz and a voltage of 10 V-80 V delivered in pulse bursts with a duration of 0.1 msec-100 msec and burst frequency of 1/sec-20/sec by an electrode with an impedance of less than 1000 Ω intravascularly to the mammal to medically treat the disease or condition, wherein the disease or condition and corresponding treatment result is selected from the group consisting of
- cancer and resulting in at least one of decreased mediastinal ingrowth, decrease in metastases, or decrease or absence of tumors;
- diabetes and resulting in at least one of decreased blood sugar levels or decreased insulin requirement;
- chronic obstructive pulmonary disease (COPD) and resulting in increased lung function;
- rheumatoid arthritis and resulting in decreased in C-reactive protein (CRP) levels; and
- osteoarthritis and resulting in decreased pain, where PRF is given before, simultaneous with or after chemical, radiation or surgical treatment.

6. A method for treating immunodeficiency in a mammal, the method comprising using a pulse generator for administering intravascular pulse radiofrequency (PRF) stimulations over a period of between 2 min and 30 min, the stimulations comprising applying a signal with a frequency of 50,000 Hz-1,000,000 Hz and a voltage of 10 V-80 V delivered in pulse bursts with a duration of 0.1 msec-100 msec and burst frequency of 1/sec-20/sec by an electrode with an impedance of less than 1000 Ω to the mammal resulting in an increased immune response in the mammal wherein the medical treatment further results in activating the immune system or relieving pain and wherein PRF is applied together with vaccination.

7. The method according to claim 1 performed using an active electrode that is an electro-catheter, with or without a steerable tip, to enable placement of the active part of the electrode closer to a target.

8. The method according to claim 7, wherein the target is a tissue, such as a solid tumor or a diseased organ, or wherein the target is the nervus vagus.

9. The method of claim 1 where the mammal is a human.

10. The method of claim 1 wherein when the disease or condition is cancer, PRF is applied in the vena brachialis and PRF parameters are 4 times per second pulses of 10 msec 420,000 Hz, 60 V for 20 minutes.

11. The method of claim 1 wherein when the disease of condition is diabetes, PRF is applied in the vena brachialis and PRF parameters are an impedance of 276 Ohms, and applied at 4×10 msec and 45 V for 20 minutes.

12. The method of claim 1 wherein when the disease or condition is COPD, PRF parameters are an impedance of 480 Ohms, and applied at 4×10 msec/sec and 60 V, during 20 minutes.

13. A method for treating immunodeficiency in a mammal, the method comprising using a pulse generator for administering intravascular pulse radiofrequency (PRF) stimulations over a period of between 2 min and 30 min, the stimulations comprising applying a signal with a frequency of 50,000 Hz-1,000,000 Hz and a voltage of 10 V-80 V delivered in pulse bursts with a duration of 0.1 msec-100 msec and burst frequency of 1/sec-20/sec by an electrode with an impedance of less than 1000 Ω to the mammal resulting in an increased immune response in the mammal where PRF is given before, simultaneous with or after chemical, radiation or surgical treatment.

14. The method according to claim 5 performed using an active electrode that is an electro-catheter, with or without a steerable tip, to enable placement of the active part of the electrode closer to a target.

15. The method according to claim 14, wherein the target is a tissue, such as a solid tumor or a diseased organ, or wherein the target is the nervus vagus.

16. The method of claim 5 where the mammal is a human.

17. The method of claim 5 wherein when the disease or condition is cancer, PRF is applied in the vena brachialis and PRF parameters are 4 times per second pulses of 10 msec 420,000 Hz, 60 V for 20 minutes.

18. The method of claim 5 wherein when the disease of condition is diabetes, PRF is applied in the vena brachialis and PRF parameters are an impedance of 276 Ohms, and applied at 4×10 msec and 45 V for 20 minutes.

19. The method of claim 5 wherein when the disease or condition is COPD, PRF parameters are an impedance of 480 Ohms, and applied at 4×10 msec/sec and 60 V, during 20 minutes.

20. The method according to claim 5 wherein the disease or condition to be treated is an inflammation related disease, an immune disease, an auto-immune disease or a disease related to allostatic load.

21. The method according to claim 20, wherein the disease or condition is selected from the group of cancer, infectious diseases, immunosuppression or immunodeficiencies.

22. The method according to claim 5, wherein the disease or condition is selected from the group of infectious diseases, in particular viral infections, and more specifically HIV infection; cancer, comprising solid tumours and blood borne tumours, such as lymphoma's, myeloma's, leukemia, breast cancer, lung cancer, head-and-neck cancers, colon cancer, pancreas cancer, prostate cancer, gastric cancer, ovarian cancer, and metastases thereof; immunosuppression, caused by chemotherapy, radiation therapy, or treatment with corticosteroids; immunodeficiency, e.g. caused by malnutrition, ageing, cancer, viral infections or (hereditary) primary immunodeficiencies like SCID, ADA deficiency, Di George's syndrome, Omenn syndrome, agammaglobulinemia, Wiskott-Aldrich syndrome, ataxia telangiectasia, ataxia-like syndrome, Nijmegen breakage syndrome, Bloom syndrome, etc.; complement deficiencies; and phagocyte disorders, such as Kostmann syndrome, neutropenia; auto-immune diseases, such as rheumatoid arthritis, alopecia areata, ankylosing sponmdylitis, autoimmune cardiopathy, autoimmune hepatitis, autoimmune pancreatitis, autoimmune inner ear disease, autoimmune progesterone dermatitis, autoimmune uveitis, Chagas disease, chronic obstructive pulmonary disease (COPD), celiac disease, cold agglutinin disease, Crohn's disease, dermatomyositis, diabetes mellitus, eosinophilic fasciitis, gastrointestinal pemphigoid, Goodpasture's syndrome, Graves' disease, Guillain-Barrésyndrome, Hashimoto's encephalitis, Hashimoto's thyroiditis, thrombocytopenic purpura, irritable bowel syndrome (IBS), Kawasaki's disease, lupus erythematosus, Miller-Fisher syndrome, mixed connective tissue disease (MCTD), morphea, multiple sclerosis, myasthenia gravis, narcolepsy, neuromyotonia, osteoporosis, pemphigus vulgaris, pernicious anaemia, polymyositis, primary biliary cirrhosis, inflammatory neuropathy, psoriasis, psoriatric arthritis, relapsing polychondritis, restless leg syndrome, sarcoidosis, schizophrenia, giant cell arthritis, ulcerative colitis, vaculitis, vitiligo, Wegner's granulomatosis; and conditions related to allostatic load like insulin resistance, metabolic syndrome, diabetes type 2, atherosclerosis, hypertension, coronary infarction, stroke, arthrosis, migraine, cognitive dysfunctions; stress related allostatic load conditions, such as depression, burn-out, chronic fatigue syndrome, fibromyalgia, post-traumatic stress syndrome, stress related sleep disorders, gastric ulcers; and trauma related allostatic load conditions, such as post-traumatic vegetative syndromes, neuropathies, phantom pain and unexplained persistent pain following trauma.

* * * * *